United States Patent
Braun et al.

(10) Patent No.: US 10,918,672 B1
(45) Date of Patent: Feb. 16, 2021

(54) SMALL TISSUE CCR5⁻MSCS FOR TREATMENT OF HIV

(71) Applicant: The Administrators of the Tulane Educational Fund, New Orleans, LA (US)

(72) Inventors: Stephen E. Braun, New Orleans, LA (US); Reza Izadpanah, New Orleans, LA (US); Eckhard Alt, New Orleans, LA (US)

(73) Assignee: THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 355 days.

(21) Appl. No.: 15/481,464

(22) Filed: Apr. 7, 2017

Related U.S. Application Data (60) Provisional application No. 62/319,657, filed on Apr. 7, 2016.

(51) Int. Cl.
| | |
|---|---|
| A61K 35/35 | (2015.01) |
| C12N 15/113 | (2010.01) |
| A61K 9/00 | (2006.01) |
| C12N 15/85 | (2006.01) |
| C12N 15/90 | (2006.01) |

(52) U.S. Cl.
CPC ............ *A61K 35/35* (2013.01); *A61K 9/0019* (2013.01); *A61K 9/0024* (2013.01); *C12N 15/1138* (2013.01); *C12N 15/85* (2013.01); *C12N 15/907* (2013.01)

(58) Field of Classification Search
None
See application file for complete search history.

(56) References Cited

U.S. PATENT DOCUMENTS

| | | |
|---|---|---|
| 9,447,379 B2 | 9/2016 | Alt |
| 2004/0067218 A1* | 4/2004 | Casteilla .............. C12N 5/0667 424/93.7 |
| 2008/0003681 A1 | 1/2008 | Bangera et al. |
| 2013/0190729 A1* | 7/2013 | Izadpanah ............ C12N 5/0619 604/522 |

FOREIGN PATENT DOCUMENTS

| | | |
|---|---|---|
| CN | 102888381 | 1/2013 |
| WO | WO2007016372 | 2/2007 |
| WO | WO 14/165825 | * 10/2014 |

OTHER PUBLICATIONS

Madhusudan et al., Clin. Cancer. Res., 2004, 10: 2986-2996.*
NordiQC, 2019.*
Hütter G., et al. Long-term control of HIV by CCR5 Delta32/Delta32 stem-cell transplantation. N Engl J Med. (2009) 360:692-8.
Krissanapong M., et al., Generation of CCR5-defective CD34 cells from ZFN-driven stop codon-integrated mesenchymal stem cell clones, Journal of Biomedical Science (2015) 22:25.
Nazai-Shafti TZ, et al. Mesenchymal stem cell derived hematopoietic cells are permissive to HIV-1 infection. Retrovirology 8:3 (2011).
Rodbell M. "Metabolism of isolated fat cells: Effects of hormones on glucose metabolism and lipolysis" J. Biol. Chem. 239 (1964) 375-380).
Ran, F. A. et al. Genome engineering using the CRISPR-Cas9 system, Nature Protocols, 2013, 8: p. 2281-2308.

* cited by examiner

*Primary Examiner* — Ileana Popa
(74) *Attorney, Agent, or Firm* — Boulware & Valoir (57) ABSTRACT

A method of curing (or at least treating) HIV, by obtaining small tissue mesenchymal stem cells (stMSC) from adipose tissue of a patient with HIV or from a syngeneic donor or an immuno-compatible donor, wherein said stMSC are i) 4-6 μm in diameter, ii) pluripotent, and iii) have CD11b⁻, CD34⁻, CD45⁻, CD 29, CD 49, Oct 4 and SSEA 4 surface markers when harvested. Preferred sources are autologous adipose tissue. Next those stMSCs are gene edited to provide CCR5⁻ stMSCs and optionally amplified by growth in culture and/or by cell selection for gene edited stMSCs and then re-introducing into the patient. Preferably, the CCR5⁻ stMSCs will re-populate the patient with stem cells that can no longer act as latent HIV reservoirs and can differentiate into immune cells that are HIV resistant. If desired, the patient can be first treated, e.g., by radiation, to destroy the bone marrow cells before the re-introduction. However, this may not be necessary for patient who already has significant destruction of immunity by HIV.

20 Claims, 3 Drawing Sheets
Specification includes a Sequence Listing.

| Targeting site | Insertion/deletion |
|---|---|
| TTCTTCATCATCCTCCTGACAATCGATAGGTACCTGGCT | |
| TTCTTCATCATCCTCCTGACAATCTCGATAGGTACCTGGCT | +TC |
| TTCTTCATCATCCTCCTGAC------CGATAGGTACCTGGCT | -AAT |
| TTCTTCATCATCCTCCTGACAATCCGATAGGTACCTGGCT | +C |
| TTCTTCATCATCCTCCTGACAATCGATAGGTACCTGGCT | |
| TTCTTCATCATCCTCCTGACAATCTCGATAGGTACCTGGCT | +TC |
| TTCTTCATCATCCTCCTGACA--TCGATAGGTACCTGGCT | -A |

Clones

SUREYOR assay for detection of CCR5-713-732
targeting site and CCR3 off-target (score 1.492). The
cells are from GFP sorting

SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence

```
<220> FEATURE:
<223> OTHER INFORMATION: Artificial sgRNA sequence

<400> SEQUENCE: 1
tcactatgct gccgcccagt ggg                                            23

<210> SEQ ID NO 2
<211> LENGTH: 23
<212> TYPE: DNA
<213> ORGANISM: Artificial Sequence
<220> FEATURE:
<223> OTHER INFORMATION: Artificial sgRNA

<400> SEQUENCE: 2
tcatcctcct gacaatcgat agg                                            23

<210> SEQ ID NO 3
<211> LENGTH: 23
<212> TYPE: DNA
<213> ORGANISM: Artificial Sequence
<220> FEATURE:
<223> OTHER INFORMATION: Artificial sgRNA

<400> SEQUENCE: 3
cctgacaatc gataggtacc tgg                                            23

<210> SEQ ID NO 4
<211> LENGTH: 23
<212> TYPE: DNA
<213> ORGANISM: Artificial Sequence
<220> FEATURE:
<223> OTHER INFORMATION: Artificial sgRNA

<400> SEQUENCE: 4
caatgtgtca actcttgaca ggg                                            23

<210> SEQ ID NO 5
<211> LENGTH: 21
<212> TYPE: DNA
<213> ORGANISM: Artificial Sequence
<220> FEATURE:
<223> OTHER INFORMATION: Artificial sgRNA

<400> SEQUENCE: 5
cctgccaaaa aatcaatgtg a                                              21

<210> SEQ ID NO 6
<211> LENGTH: 20
<212> TYPE: DNA
<213> ORGANISM: Artificial Sequence
<220> FEATURE:
<223> OTHER INFORMATION: Artificial sgRNA

<400> SEQUENCE: 6
aggaccagcc ccaagatgac                                                20

<210> SEQ ID NO 7
<211> LENGTH: 20
<212> TYPE: DNA
<213> ORGANISM: Artificial Sequence
<220> FEATURE:
<223> OTHER INFORMATION: Artificial sgRNA

<400> SEQUENCE: 7
gcaaattggg gcccaactcc                                                20
```

```
<210> SEQ ID NO 8
<211> LENGTH: 26
<212> TYPE: DNA
<213> ORGANISM: Artificial Sequence
<220> FEATURE:
<223> OTHER INFORMATION: Artificial sgRNA

<400> SEQUENCE: 8
ccaaaatgtt cctcattatt gtgtgg                                              26

<210> SEQ ID NO 9
<211> LENGTH: 20
<212> TYPE: DNA
<213> ORGANISM: Artificial Sequence
<220> FEATURE:
<223> OTHER INFORMATION: Artificial sgRNA

<400> SEQUENCE: 9
tgtgggcctc ttgggcaatg                                                     20

<210> SEQ ID NO 10
<211> LENGTH: 24
<212> TYPE: DNA
<213> ORGANISM: Artificial Sequence
<220> FEATURE:
<223> OTHER INFORMATION: Artificial sgRNA

<400> SEQUENCE: 10
cagaagatgg tcattctcag agtg                                                24
```

SMALL TISSUE CCR5⁻MSCS FOR TREATMENT OF HIV

PRIOR RELATED APPLICATIONS

This application claims priority to U.S. Ser. No. 61/319,657, filed Apr. 7, 2016, which is incorporated by reference in its entirety for all purposes.

FEDERALLY SPONSORED RESEARCH STATEMENT

Not applicable.

FIELD OF THE DISCLOSURE

The disclosure generally relates to novel compositions of mesenchymal stem cell (MSC) constructs and to methods of treatment for HIV-1 using engineered MSCs.

BACKGROUND OF THE DISCLOSURE

For a long time it was assumed by the medical community that the bone marrow is the source of stem cells—that bone marrow was the "vault" of stem cells. At the end of 90s, Darwin Prokop's group isolated a subpopulation of stem cells from the bone marrow that showed characteristics of mesenchymal cells, called mesenchymal stem cells or mesenchymal stromal cells (MSCs).

The primary identification of MSCs was made through their ability to adhere to plastic on a cell culture dish. The last ten years have intensively focused on research on those bone marrow derived stem cells and it has been shown that a few of those cells have true multipotency demonstrated by their capacity to differentiate into endoderm, ectoderm and mesoderm lineages. In other words, culturing of these cells under lineage specific inducing media is able to induce some of these cells to an adipogenic, osteogenic, chondrogenic, neurogenic, or hepatogenic differentiation.

Bone marrow derived stem cells have been extensively characterized and it has been found that cultured MSCs are positive for CD44, CD90, CD105 and CD73 and this has been established as the definition of mesenchymal multipotent stem cells by the medical community.

In addition to the finding that the bone marrow contains mesenchymal stem ells, recent publications over the years have provided wealth of evidence that in addition to bone marrow, stem cells reside in many other organs, including adipose tissue, heart, skin, brain, hair follicles, liver, and pancreas.

However, there is still a considerable confusion as to the hierarchy of stem cells and the term "stem cell" and "multipotent stem cells" or "mesenchymal stem cells" are still not clearly defined, nor understood on a broad basis. In current terminology, a large group of progenitor cells is falsely labeled as stem cells.

Progenitor cells are those stem cells that have already initiated a specific lineage committed differentiation pathway and have determined in their differentiation pathway to go this route into a terminally differentiated cell. Recently several articles have tried to more closely define the truly mesenchymal stem cells, which carry pluripotent stem cell characteristics and have not yet begun a differentiation to a certain lineage.

However, the correct meaning of different cell surface markers is still not fully understood. This is due to the transitional nature of surface marker expression. For example, in a freshly obtained culture of bone marrow derived stem cells or of tissue derived stem cells such as adipose tissue derived stem cells, initially a number of 30-65% roughly is CD34 positive. Upon culturing, this fraction is nearly completely lost. On the other hand, CD105 initially is present only in about 20-25% of cells. Upon culturing in fetal bovine serum (FBS) virtually more than 90% of the cells become positive for CD 105.

A good deal of the uncertainty about stem cell surface markers is thus due to the fact that the surface antigens change on culturing, moving forward or backwards in the developmental lineage. Thus, the expression of surface markers highly depends on media, culture conditions, type of cell culture dish, and the status of passages the cells have undergone.

While all these facts explain the difficulty and confusion in defining early mesenchymal stem cells, research by the present inventors has evidenced that the early mesenchymal stem cells are ubiquitously distributed throughout the body in small blood vessels. While there are several publications have postulated that pericytes would be the early stem cells, our data and evidence suggest that while the pericytes are very close relatives of the early stem cells, they are not the true mesenchymal stem cells.

We have found that the early mesenchymal stem cells are small cells—smaller than 6 µm diameter with a small cytoplasm compared to the nucleus and that these cells can be as small as 4 µm and less in diameter. The cells are located in the vessel within the wall of the small pre- and post-capillary vessels and of all arteries, attached opposite the luminal side of the lamina elastica interna, or in other words, outside of the elastic internal lamina. The endothelial cells are attached to the luminal side of this lamina.

These early mesenchymal cells have a silencing inhibition due to their integrin binding ($\alpha 5\beta 1$) to the extra-cellular matrix that induces a contact inhibition, and this inhibition makes those cells dormant. In fact, 99.5% of these early stem cells are in a $G_0$ (G zero) phase indicating that there is no protein synthesis or any active replication. SPARC or another specific protease is able to release those cells from their extra-cellular matrix contact inhibition and hibernation.

Due to their possession of the surface markers of CXCR4 receptor (corresponding to the SDF1 ligand) and a hepatocyte growth factor receptor, the cells are able to respond to stimuli from the tissue and migrate. Their small size enables them to easily penetrate either in an intravascular direction into the circulation or an extravascular direction into the tissue.

In addition, recent research at our lab has evidenced that these cells are the source of all further tissue resident progenitor cells and can, independent from their original location in a specific organ or tissue, differentiate into all three lineages. Further, they are able to differentiate into hematopoietic lineages. Therefore, according to our data the bone marrow should no longer be considered the vault of stem cells; but rather the small early pluripotent stem cells are in the blood vessels in all tissues and in organs such as the heart, brain, kidney, skin, adipose tissue, and so on.

Evidence and research in our lab has also shown that upon treatment of these early stem cells with a simulating factor containing Interleukin 1 (IL1), IL10, and macrophage stimulating factor, a conversion of the early pluripotent stem cells into cells of hematopoietic lineage can be induced. By addition of EPO and other growth factors lymphoid and erythropoetic differentiation can be induced, indicating that these cells are fully capable to replace bone marrow, thereby reinitiating a functional immune system.

Recognition of these cells as tissue resident stem cells, as well as being the latent HIV reservoir cells provides new treatment opportunities. The ability to replace bone marrow stem cells with such cells has opened new treatment modalities for HIV. This application addresses those inventions.

SUMMARY OF THE INVENTION

We have determined that small, tissue resident multipotent mesenchymal stromal cells (stMSCs) have the potential to differentiate to hematopoietic cells. Proof of principal studies utilized clonally isolated adipose tissue derived adherent MSCs cells that displayed a cell surface CD11b$^-$, CD34$^-$, CD45$^-$, CD 29, CD 49, Oct 4 and SSEA 4 phenotype to evince the hematopoietic potential of such cells by eliminating the potential for derivation from contaminating hematopoietic stem cells from the peripheral blood.

We isolated these cells from adipose tissue, which also contains some blood vessels and these small 4-6 μm stem cells. Such adipose derived SC provide a new and readily available method of generating cells of the hematopoietic system that can be used for autologous transplant thus obviating the need for bone marrow transplant with its inherent risk of reintroducing occult malignant cells. The treatment strategy disclosed herein, in which adipose tissue resident stem cells from patients with hematopoietic malignancy will be used to replace malignant hematopoietic cells in an autologous engraftment, will avoid the onset of relapse in autologous transplantation and avoids the need for allogeneic transplantation with its risk of graft versus host disease.

We use gene editing to disrupt or knockout the CCR5 gene of these stMSCs and then replace or augment the patient's own stem cells with these genetically modified autologous stem cells that are made HIV virus replication deficient by the homozygous disruption or knock-out of the CCR5 gene.

C—C chemokine receptor type 5, also known as CCR5 or CD195, is a protein on the surface of white blood cells that is involved in the immune system as it acts as a receptor for chemokines. This is the process by which T cells are attracted to specific tissue and organ targets. Many forms of HIV, the virus that causes AIDS, initially use CCR5 to enter and infect host cells. Certain individuals carry a mutation known as CCR5-→32 in the CCR5 gene, protecting them against these strains of HIV. Thus, cells containing a knockout or deletion mutant of CCR5 will be able to evade HIV infection and will prevent the formation of new latent HIV reservoirs.

CCR5$^-$ stem cells can be re-introduced into the body, thus populating the body, and on differentiation, eventually replacing the patient's own immune cells that are subject to HIV attack, with cells that no longer allow the entry of HIV. Further, even when undifferentiated, new latent HIV reservoirs will not form, allowing the eventual elimination of the virus in its entirety. Modification of the CCR5 gene not only interferes with the ability of the cells to take up the virus, as is publicly known, but also prevents the virus from replicating. Indeed, the first patient cured with a bone marrow transplant of CCR5 negative cells has already been reported (Hutter 2009).

Stem cells are harvested and isolated from the patient's own body as described herein. By subjecting the cells to a gene editing of the CCR5 gene in a homozygous manner by, e.g., CRISPR/CAS9 editing, the gene edited cells become resistant to virus infection, without interfering with other significant and critical cell functions.

It is important to selectively modify only the CCR5 gene without affecting any other genes, especially those genes directly neighboring on the chromosome such as CCR 2, 3 or 4, as these genes take over the function of the mutated and non-functional CCR5 gene in normal cell physiology and thus are needed for functionality.

Depending on the efficiency of transfection and especially the efficiency of the CRISPR guide RNA targeting molecules, diploid target cells could have one, both, or neither CCR5 genes mutated. Our CCR5 guide sequences were shown to be very efficient in targeting the CCR5 gene.

To evaluate the potential for off target activity, we also evaluated CCR5 mutagenesis of the CCR2 and CCR3 genes, which are quite homologous to CCR5. After transfection with the CRISPR and CCR5 guide sequences, genomic DNA was isolated and CCR2 and CCR3 genes were amplified and subjected to surveyor assay. We did not detect any modification in either CCR2 or CCR3, nor did we isolate any CCR2 clones with mutated sequences. These data demonstrate undetectable levels of toxicity to other homologous chemokine receptor genes.

Transfected stMSC have extensive proliferation capacity. The CCR5$^-$ cells will be expanded ex vivo under GMP conditions. Patients with viral suppression due to HAART will receive repeated infusion of the CCR5 deficient cells. These cells are expected to populate the body and replace lost T cells with HIV resistant T cells, thus effecting a "cure" for HIV.

"Adult stem cells" are typically multipotent stem cells derived from a non-infant person, and does not imply any particular age of the donor. Also known as somatic stem cells, they can be found in children, as well as adults.

As used herein, "autologous" means cells derived from the patient and "syngeneic" means derived from a nearly genetically identical patient, such as a twin or clone. "Allogeneic" refers to cells derived from the same species, but having a different genotype. The preferred stMSCs are autologous or syngeneic, but immune-compatible cells could also be used.

As used herein "small tissue-derived MSCs" or "stMSCs" are 4-6 μm diameter cells isolated from tissues, adjacent the lumina of blood vessels, that are pluripotent and can be induced to differentiate into immune cells. These cells have a phenotype of CD11b$^-$, CD34$^-$, CD45$^-$, CD 29, CD 49, Oct 4 and SSEA 4 when harvested.

These stMSCs can either be used in a mixed population including regeneration cells, or they can be enriched for stMSCs containing these markers, e.g., by FACS cell sorting, or enriched by size selection, selection for adherence to a feeder layer, combinations thereof, and the like. The cells can also be amplified before use. These steps can be done before or after CRR5 editing, or both. In one preferred method, the cells are edited and the cells then selected based on a marker included with the gene editing, and these are then amplified before use, ensuring a population that is highly enriched for CCR5 negative stMSCs. However, enrichment is not essential, particularly where autologous cells are used.

As used herein "pericytes" are defined contractile cells that wrap around the endothelial cells that line the capillaries and venules throughout the body. stMSCs can be distinguished from pericytes by their size, markers, and multilineage potential.

As used herein, "CCR5" or C—C chemokine receptor type 5 or CD195, is a protein on the surface of white blood cells that is involved in the immune system as it acts as a receptor for chemokines. It is also the receptor for many strains of HIV entry into cells.

"CCR5-Δ32" (or CCR5-D32 or CCR5 delta 32) is a natural allele of CCR5 that is a 32-base-pair deletion that introduces a premature stop codon into the CCR5 receptor locus, resulting in a nonfunctional receptor.

"CCR5$^-$" is a knockout mutant of CCR5 that has no detectable HIV entry capability.

HIV1 most commonly uses the chemokine receptors CCR5 and/or CXCR4 as co-receptors to enter target immunological cells. "CXCR-4" is an alpha-chemokine receptor specific for stromal-derived-factor-1 (SDF-1 also called CXCL12), a molecule endowed with potent chemotactic activity for lymphocytes. CXCR4 is one of several chemokine receptors that HIV can use to infect CD4+ T cells.

CCR5 is a target for CRISPR knockout because the natural Δ32 mutation does not cause significant immunological deficiencies, but CXCR4 is not a target for CRISPR knockout because the function is required for normal stem cell function.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention. Elements of this type would include e.g., buffers, chelators, nutrients, instructions for use, and the like.

The following abbreviations are used herein:

| ABBREVIATION | TERM |
|---|---|
| ADST | Adipose derived stem cells |
| ART | antiretroviral therapy |
| cDNA | Copy DNA |
| DNA | Deoxyribonucleic acid |
| FBS | Fetal bovine serum |
| HAART | Highly active antiretroviral therapy—HAART is a customized combination of different classes of medications based on such factors as the patient's viral load, viral strain, CD4+ cell count, and disease symptoms. |
| Indel | Insertion/deletion |
| MEM | Minimum-essential medium |
| PBS | Phosphate buffered saline |
| PCR | Polymerase chain reaction |
| qPCR | Quantitative PCR |
| RNA | Ribonucleic acid |
| αMEM | MEM with Earles balanced Salts, contains non-essential amino acids, sodium pyruvate,and additional vitamins. |

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

FIG. 1 shows a comparison of CCR5 targeting mutation of CRISPR-Cas9 system on different targeting sites in 293T cells. Cells were transfected with CRISPR plasmids co-expressing various guide RNA sequences. Genomic DNA was subsequently harvested, used to amplify the CCR5 sequences, and subjected to surveyor assay. The surveyor nuclease is part of a family of mismatch-specific endonucleases that were discovered in celery and which recognizes all base substitutions and insertions/deletions, and cleaves the 3' side of mismatched sites in both DNA strands with high specificity. It can thus be used to identify and analyze mutations in a variety of organisms and cell types. The data shows that most of the CCR5 sequences were mutated by the CRISPR treatment.

FIG. 4 Analysis of Indel mutations with CRISPR-Cas9 system in human ASC #207 cells. Since the cleavage of DNA by Cas9 leaves behind characteristic short insertion/deletion (Indel) mutations, we analyzed the sequence of the CCR5 gene from the gRNA-transduced MSCs. Total genomic DNA was isolated from cells sorted to be positive for GFP and PCR was conducted as above to amplify the targeting region of CCR5 with genomic DNA. The PCR products were cloned into the TA cloning vector pCR4-TOPO and colonies sequenced. Here are representative sequences of mutated alleles identified. Red dashes, deleted bases; red bases, insertions or mutations.

FIG. 6 shows the results of the surveyor assay for detection of CCR5 targeting with two CCR5 guide RNA. A. Expected band sizes. If targeting site #101 were functional, the surveyor assay would generate bands of 358 and 200 bps. If the targeting site #103 were functional, the surveyor assay would generate bands of 257 and 301 bps. if both were functional, bands of 257 and 200 would be generated. Additionally, a shorter PCR product (instead of the full-length PCR product) would also be generated from deletion of sequences between the #101 and #103 double-stranded breaks, which is visible in the treated sample. These data indicate that both the #101 and #103 targeting sequences are functional and that the efficiency of each individually is not complete; however, the combination of both targeting sequencing in the duel vector increases the overall efficiency of the system.

DETAILED DESCRIPTION OF THE INVENTION

In about 2005, the first hint arose that the 4-6 μm diameter tissue derived MSCs cells—herein called stMSCs—are not plastic adherent like the conventional fibroblast-like stem cells or fibroblasts. Instead, the stMSCs use fibroblastic cells adhering to the culture dish as a feeder layer.

An infection of HIV virus in these cell cultures and the addition of retroviral drugs clearly demonstrated that the virus was eradicated in all plastic adherent cells and no virus replication could then be measured in those cell cultures. However, upon addition of lymphocytes, the infection returned and the small round 4-6 μm cells sitting on the otherwise plastic adherent spindle shaped stem cells were discovered to be the carrier of the dormant virus genome, as evidenced by nested PCR. Nazai-Shafti (2011).

Since the virus cannot replicate itself in these small cells and the cells are in $G_0$ phase, typical HIV drugs are less effective against these latent HIV-infected stem cells. Even when the cells start proliferating due to their nature as stem cells, they exhibit very high level of ABC cassette transporters, which significantly reduces the intracellular content of retroviral drugs. Thus, they are difficult to eradicate using conventional therapies.

The infection returns after initially being undetectable by two ways: First, when the early stem cells begin to differentiate, the virus also replicates and spreads into other cells where it further replicates. Second, when these early stem cells differentiate into a macrophage lineage, they demonstrate small protrusions of the cellular membrane that shed off as exosomes (or microsomes), that have a diameter of about 90 to 150 nanometer. These exosomes contain RNAs and especially mRNA, and non-coating RNAs among other phenomena. It has been shown that the exosomes are phagocytosed by other calls, including macrophages, and the genetic material is exchanged between cells in a way that also enables the virus to spread.

This explains why it is difficult to cure HIV. Lymphopoetic differentiation of the early stMSCs (which represent the reservoir for the virus) and the release and uptake of the exosomes containing the virus is the mechanism whereby disease can return upon cessation of antiviral drug therapy making HIV currently a treatable, but not curable disease.

By interfering with the ability of virus replication on a genetic level would be a method to possibly cure, and thereby eradicate HIV infection. The herein described novel therapy consists of a replacement of the patient's own intrinsic early stem cells with genetically modified autologous stem cells that are made HIV virus replication deficient by a homozygous knock-down or knock-out of the CCR5 gene.

These CCR5⁻ stem cells can be introduced into the body, thus populating the body, and on differentiation eventually replace the patient's own immune cells that are subject to HIV attack, with cells that no longer allow the entry of HIV since the CCR5 is defective or missing. Modification of the CCR5 gene not only interferes with the ability of the cells to take up the virus, as is publicly known, but also prevents the virus from replicating. Indeed, the first patient cured with a bone marrow transplant of CCR5 negative cells has already been reported (Hutter 2009). In one embodiment, the CCR5⁻ stMSCs is re-introduced into the body by surgical incision.

When the connective tissue of adipose tissue is digested, such as with collagenase, the lipid containing adipocytes can be separated from the other cell types. In 1964, Rodbell reported the use of collagenase to dissociate adipose tissue into a cellular suspension that could then be fractionated by centrifugation into an upper, lipid-filled adipocyte fraction, and a cell pellet comprised of non-lipid-filled cells. The pelleted non-adipocyte fraction of cells isolated from adipose tissue by enzyme digestion has been termed the "stromal vascular cell" or SVF population.

Heretofore, adipocytes have been separated from the SVF by centrifugation wherein the adipocytes float and the cells form the SVF pellet. Typically however, the SVF is typically subject to further processing and selection, including plastic adherence. Cells from the stromal vascular fraction that have been subject to plastic adherence are typically referred to as cultured stromal vascular cells, stromal cells, "adipose tissue-derived stromal cells" and "adipose tissue-derived stem cells" (ADSC or ASC), adipose derived mesenchymal stem cells (AD-MSC), or the preferred small tissue mesenchymal stem cells (stMSC). Not withstanding other definitions that may exist in the art, as used herein, the term "stromal vascular fraction" or "SVF" cells refers to all of the constituent cells of adipose tissue after enzyme digestion and removal of adipocytes and are not limited to plastic adherent cells.

One protocol for isolating adipose derived stem cells is as follows, but of course variations are possible. Adipose tissue is collected by needle biopsy or liposuction aspiration. The tissue sample is washed extensively with e.g., phosphate-buffered saline (PBS) containing 5% Penicillin/Streptomycin (P/S). Upon removal of debris, the sample is minced and placed in a sterile tissue culture plate with 0.075% Collagenase Type I prepared in PBS containing 2% P/S for tissue digestion. This is incubated for e.g., 30 min at 37 C, 5% CO2, and then the Collagenase Type I activity neutralized by adding 5 ml of α-MEM containing 20% heat inactivated fetal bovine serum (FBS, Atlanta Biological, Atlanta, Ga.) to the tissue sample.

The stromal vascular fraction (SVF), containing the ASCs, is obtained by centrifuging the sample at 2000 rpm for 5 min. The samples are shaken them vigorously to thoroughly disrupt the pellet and to mix the cells. This completes the separation of the stromal cells from the primary adipocytes, and the centrifugation step is repeated. After spinning, the collagenase solution above the pellet is discarded and the pellet resuspended in 1 ml buffer, incubated for 10 min on ice, washed with 20 ml of PBS/2% P/S and centrifuged at 2000 rpm for 5 min. The supernatant is aspirated, the cell pellet is resuspended in a maximum of 3 ml of stromal medium (alpha-MEM, Mediatech, Herndon, Va.) supplemented with 20% FBS, 1% L-glutamine (Mediatech), and 1% penicillin/streptomycin (Mediatech) and the cell suspension is filtered through a suitable cell strainer, and again washed. Cells can be further selected for use based on the markers discussed above, but again are not limited to plastic adherent cells. Thus, plastic adherence selection is not performed.

Single-guide RNAs (sgRNAs) used in this study were designed according to the CRISPR Design Tool (crispr.mit.edu), including Top-ranked single-guided RNAs of human CCR5 locus-specific targeting before mutation site of CCR5-Δ32 were selected.

100 SEQ ID NO. 1: TCACTATGCTGCCGCCCAGTGGG

101 SEQ ID NO. 2: TCATCCTCCTGACAATCGATAGG

102 SEQ ID NO. 3: CCTGACAATCGATAGGTACCTGG

103 SEQ ID NO. 4: CAATGTGTCAACTCTTGACAGGG

Oligonucleotides were annealed to generate double stranded DNA fragments and ligated into the BbsI digested plasmid px458 containing Cas9 and the sgRNA scaffold. The sequence of the resulting plasmids was verified by sequencing.

Genomic DNA of transfected 293T cells with plasmids were extracted 48 hours after transfection. For transfection of mesenchymal stem cells (MSCs), the Neon Transfection System was used. 20 μg of plasmid DNA in 5×10$^5$ cells were used per electroporation with pulse voltage V, pulse width 10 ms, pulse number 3 and tip type 100 μL, Cells were sorted by flow cytometry for GFP positive cells 48 hours post transfection and collected for genomic DNA extraction.

The regions of CCR5 gene that had been targeted were amplified by PCR using flanking primers SEQ ID NO. 5: 5'-CCTGCCAAAAAATCAATGTGA-3' and SEQ ID NO. 6: 5'-AGGACCAGCCCCAAGATGAC-3'. At the same time, we also amplified CCR2 and CCR3 for off-target analysis. Primers SEQ ID NO. 7: 5'-GCAAATTGGGGCC-CAACTCC-3' and SEQ ID NO. 8: 5'-CCAAAATGTTCCT-CATTATTGTGTGG-3' were used for CCR2. Primers SEQ ID NO. 9: 5'-TGTGGGCCTCTTGGGCAATG-3' and SEQ ID NO. 10: 5'-CAGAAGATGGTCATTCTCAGAGTG-3' were used for CCR3.

The purified PCR products were used for formation of heteroduplexes and subjected to Surveyor nuclease digestion. We analyzed the sequence of the CCR5 gene from the gRNA-transduced MSCs. On the other hand, the purified PCR products from genomic DNA of sorted GFP positive MSCs were cloned into the TA cloning vector pCR4-TOPO and colonies were sequenced at random.

CCR5 is an essential co-receptor for human immunodeficiency virus type 1 (HIV-1) entry. Individuals with a CCR5$^{\Delta 32}$ variant are resistant to HIV-1 infection, making CCR5 an attractive target for drug and genetic intervention against HIV-1. Previously, it has been shown that mesenchymal stem cells (MSCs) that lack expression of CCR5 are able to differentiate into cells with hematopoietic characteristics, including expression of CCR5. Therefore, CCR5 knockout mesenchymal stem cells contain the potential for use in HIV-1 treatment.

The CRISPR/Cas9 system has been recently harnessed as a novel nuclease system for genomic editing in mammalian cells. In the present study, CCR5 was knocked out using CRISPR/Cas9 system. Following design of a panel of top-ranked single-guided RNAs (sgRNAs) targeting the ORF of CCR5, we demonstrate that CRISPR/Cas9 efficiently mediates the editing of the CCR5 locus in 293T cells (ATCC® CRL-3216™) with three different sgRNAs. The 293T cell line, originally referred as 293tsA1609neo, is a highly transfectable derivative of human embryonic kidney 293 cells, and contains the SV40 T-antigen. It is used for proof of concept of the gene editing portion of the work.

Figure 1:
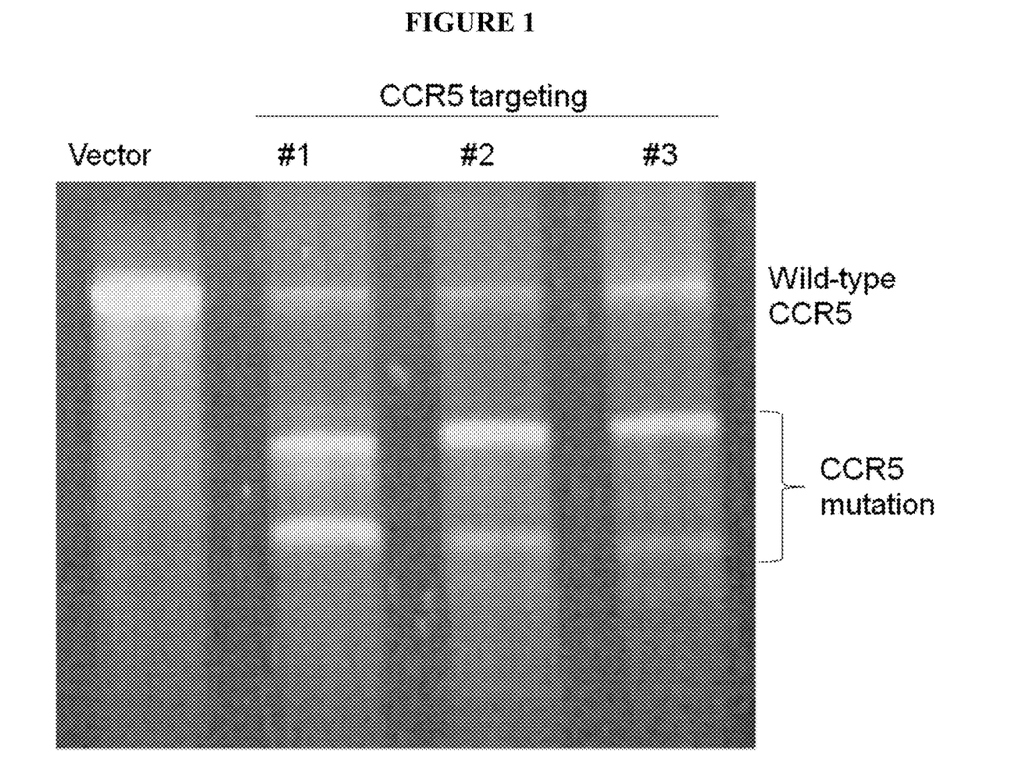
Figure 2:
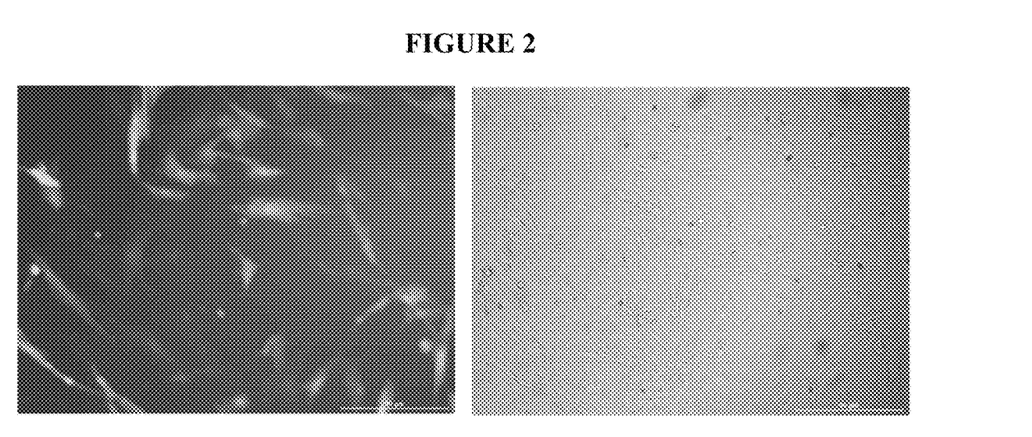
FIG. 2 shows human adipose-derived stem cells #207 (P6) transfection with neon. The left panel shows expression of GFP after transfection of the ASCs with the CRISPR plasmids. The right panel shows the ASC with a light-phase microscope.
Figure 3:
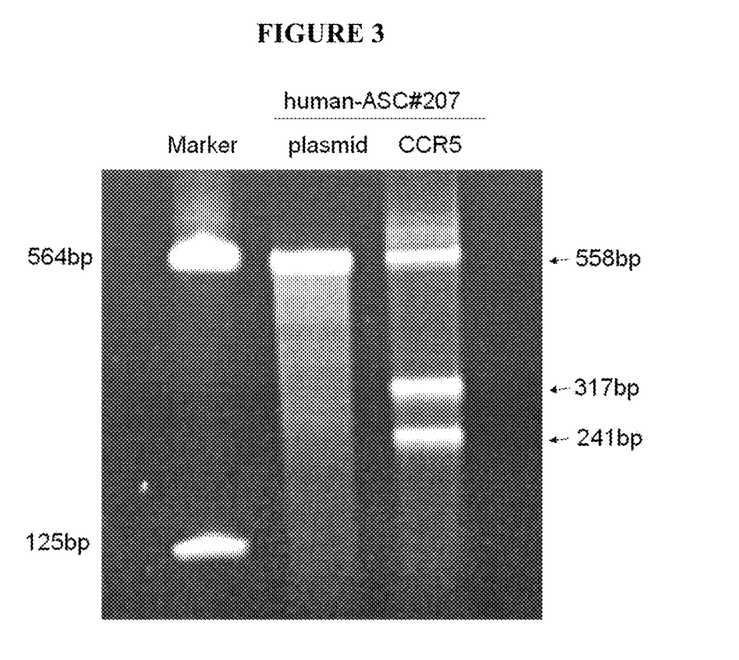
FIG. 3 shows results of the surveyor assay for detection of CCR5-713-732 (#2) targeting site in ASC cells after GFP sorting. Genomic DNA from these cells was subsequently harvested, used to amplify the CCR5 sequences, and subjected to surveyor assay. The control treated cells (Lane 2) retained only the normal sequence (558 bps fragment), while most of the CCR5 sequences in the CRISPR treatment (Lane 3) were mutated (317 and 241 bps fragments).
Figure 4:
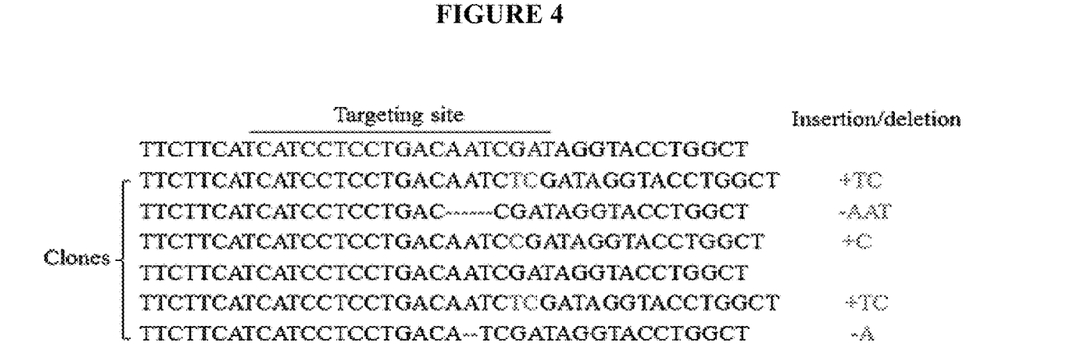
Figure 5:
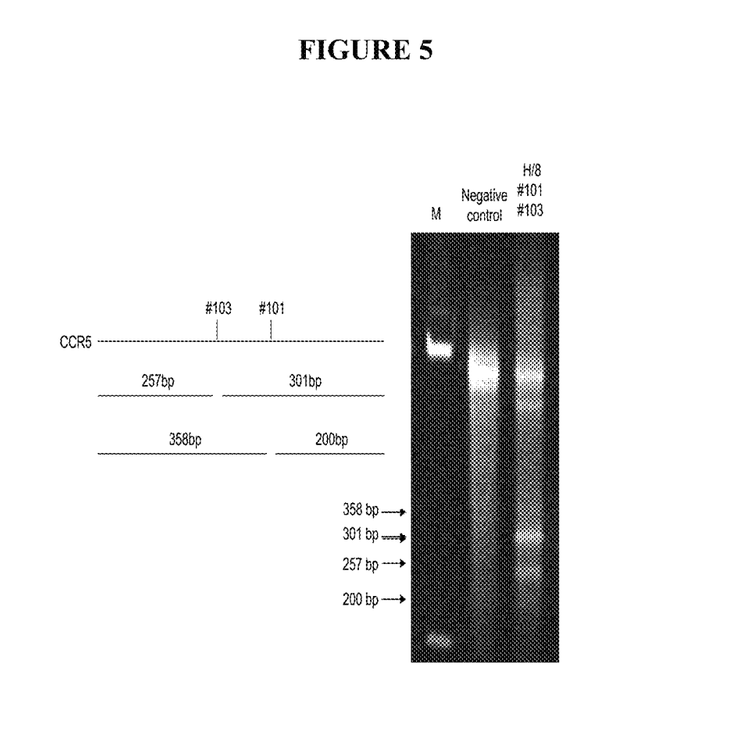
FIG. 5. shows the results of the surveyor assay for detection of CCR5 targeting and the potential for off target activity against a homologous gene (CCR3). While most of the CCR5 sequences were mutated, no mutations were detectible in the CCR3 gene. Thus, these targeting vectors do not demonstrate off target toxicity.
Figure 6:
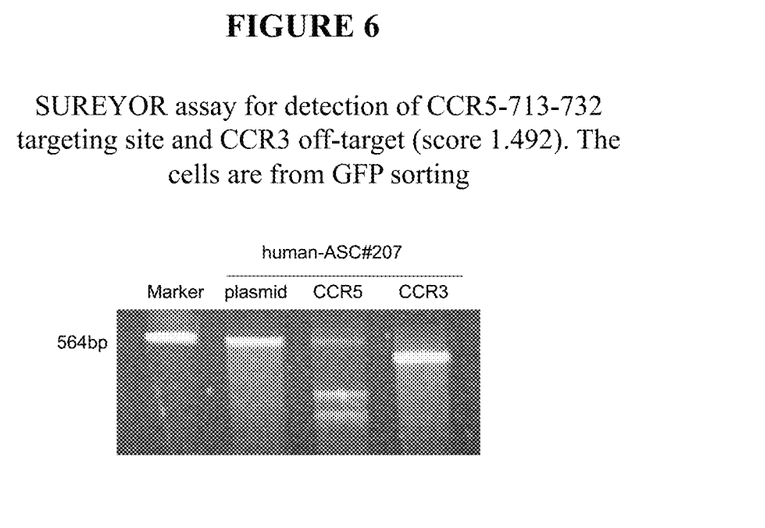

We selected the targeting site that showed the highest mutation efficiency to target CCR5 in MSCs using a neon transfection system. Our results (not shown) indicate that the transfection efficiency of MSCs is 48% as indicated by GFP-positive cell analysis. To assess for frequency of indel mutations at the target site, TOPO TA Cloning of PCR amplicons was performed and sequenced. The results showed that indel mutation efficiency of target site mediated by CRISPR/Cas9 was about 70%.

We used 293T for the surveyor assay, and MSC for the surveyor assay and for the CCR5 cloning and sequencing.

Taken together, our results demonstrate that CRISPR/Cas9 can efficiently mediate the editing of the CCR5 locus in MSCs, resulting in knockout of CCR5, which paves the way to treat HIV-1-infected patients with CCR5 knockout stMSCs, which can differentiate into HIV-1 resistant hematopoietic stem cells even with the mutated CCR5.

In the past year, we have used a lentiviral vector with 2 guide RNA targeting the CCR5 gene. With this system, the frequency of mutagenesis would result from the mutagenesis from each guide RNA AND the mutagenesis that results from deletion of the intervening sequence. Our preliminary results suggest that we can significantly increase the frequency of CCR5 mutagenesis. We are currently cloning and sequencing these mutations to verify the increase frequency.

If the frequency of gene transfer and of CRISPR-directed mutagenesis is highly efficient, then the need to select gene edited stMSCs will be diminished.

Our future work will require actual testing in human patients to confirm that the stMSCS with CCR5 knockouts can repopulate the body with healthy stem cells that can differentiate and eventually replace the patients lost T cells. Since the new cells will be CCR5 negative, they cannot be attacked by the same strain of HIV.

Each of the following is incorporated by reference herein in its entirety for all purposes.

Witter G., et al. Long-term control of HIV by CCR5 Delta32/Delta32 stem-cell transplantation. N Engl J Med. (2009) 360:692-8.

Krissanapong M., et al., Generation of CCR5-defective CD34 cells from ZFN-driven stop codon-integrated mesenchymal stem cell clones, Journal of Biomedical Science (2015) 22:25.

Nazai-Shafti T Z, et al. Mesenchymal stem cell derived hematopoietic cells are permissive to HIV-1 infection. Retrovirology 8:3 (2011).

Rodbell M. "Metabolism of isolated fat cells: Effects of hormones on glucose metabolism and lipolysis" *J. Biol. Chem.* 239 (1964) 375-380).

Ran, F. A. et al. Genome engineering using the CRISPR-Cas9 system, Nature Protocols, 2013, 8: p 2281-2308.

U.S. Pat. No. 9,447,379 DERIVATION OF HEMATOPOIETIC CELLS FROM ADULT MESENCHYMAL STEM CELLS

WO2007016372 METHOD FOR REGENERATING AN IMMUNE SYSTEM.

US20080003681 METHODS FOR ALTERING CELLULAR SUSCEPTIBILITY TO INFECTION

CN102888381 RECOMBINANT CCR5[DELTA]32 GENOTYPE EMBRYONIC STEM CELL STRAIN AND PREPARATION METHOD THEREOF

The invention claimed is:

1. A method of treating HIV infection, comprising:
   a. isolating small tissue mesenchymal stem cells (stMSCs) from a patient with HIV, from a syngeneic donor, or from an immuno-compatible donor, wherein the isolating step selects only stMSCs having the phenotype $CD11b^-CD34^-CD45^-CD29^+CD49^+Oct4^+SSEA4^+$, and
   wherein said selected stMSCs are i) 4-6 µm in diameter, and ii) pluripotent;
   b. editing the CCR5 gene in said selected stMSCs to provide $CCR5^-CD11b^-CD34^-CD45^-CD29^+CD49^+Oct4^+SSEA4^+$stMSCs; and
   c. re-introducing said $CCR5^-CD11b^-CD34^-CD45^-CD29^+CD49^+Oct4^+SSEA4^+$stMSCs into said HIV patient.

2. The method of claim 1, wherein said $CD11b^-CD34^-CD45^-CD29^+CD49^+Oct4^+SSEA4^+$stMSCs are isolated from adipose tissue.

3. The method of claim 1, wherein said $CD11b^-CD34^-CD45^-CD29^+CD49^+Oct4^+SSEA4^+$stMSCs are isolated from the adipose tissue of said HIV patient.

4. The method of claim 1, wherein said $CD11b^-CD34^-CD45^-CD29^+CD49^+Oct4^+SSEA4^+$stMSCs are isolated from adipose tissue by collagenase digestion, and not by plastic adherence selection.

5. The method of claim 1, wherein said re-introducing step is by systemic injection.

6. The method of claim 1, wherein said re-introducing step is by surgical incision and placement.

7. The method of claim 1, wherein said CCR5 gene-edited stMSCs are cultured for a period of time to grow additional $CCR5^-CD11b^-CD34^-CD45^-CD29\ CD49^+Oct4^+SSEA4^+$stMSCs for said re-introducing step.

8. The method of claim 7, wherein said $CCR5\ CD11b^-CD34^-CD45^-CD29^+CD49^+Oct4^+SSEA4^+$stMSCs are cultured in α-MEM containing fetal bovine serum.

9. The method of claim 1, wherein said $CCR5\ CD11b^-CD34^-CD45^-CD29^+CD49^+Oct4^+SSEA4^+$stMSCs are made with a CRISPR/CAS9 gene editing system.

10. The method of claim 9, wherein CRISPR/CAS9 gene editing system uses a guide RNA comprising a sequence selected from:
    i. SEQ ID NO. 1: TCACTATGCTGCCGCCCAGTGGG,
    ii. SEQ ID NO. 2: TCATCCTCCTGACAATCGATAGG,
    iii. SEQ ID NO. 3: CCTGACAATCGATAGGTACCTGG, and
    iv. SEQ ID NO. 4: CAATGTGTCAACTCTTGACAGGG.

11. A method of curing HIV infection, comprising:
    a) isolating small tissue mesenchymal stem cells (stMSCs) from a patient with HIV, from a syngeneic donor, or from an immuno-compatible donor, wherein the isolating step selects only stMSCs having the phenotype $CD11b^-CD34^-CD45^-CD29^+CD49^+Oct4^+SSEA4^+$, and
    wherein said selected stMSCs are i) 4-6 Lm in diameter, and ii) pluripotent;
    b) editing the CCR5 gene in said selected stMSCs to provide $CCR5^-CD11b^-CD34^-CD45^-CD29^+CD49^+Oct4^+SSEA4^+$stMSCs;
    c) amplifying said $CCR5^-CD11b^-CD34^-CD45^-CD29^+CD49^+Oct4^+SSEA4'$ stMSCs by growth in culture;
    d) re-introducing said amplified $CCR5\ CD11b^-CD34^-CD45^-CD29^+\ CD49^+Oct4^+\ SSEA4^+$stMSCs into said HIV patient;
    wherein said amplified $CCR5^-CD11b^+\ CD34^-CD45^-CD29\ CD49^+Oct4^+SSEA4$ stMSCs repopulate the immune system of said HIV patient with stem cells that do not harbor latent HIV reservoirs and immune cells that are resistant to HIV infection.

12. The method of claim 11, wherein said method includes separating said CCR5$^+$CD11b$^-$CD34 CD45$^-$CD29$^+$CD49$^+$Oct4$^+$SSEA4$^+$stMSCs from CD11b$^-$CD34$^-$CD45$^+$CD29$^+$CD49$^+$Oct4$^+$SSEA4$^+$stMSCs before said amplifying step c), after said amplifying step c), or both before and after said amplifying step c).

13. The method of claim 11, wherein the bone marrow of said patient is irradiated to destroy endogenous cell before said reintroducing step.

14. The method of claim 11, wherein said CD11b$^-$CD34$^-$CD45$^-$CD29$^+$CD49$^+$Oct4$^+$SSEA4$^+$stMSCs are isolated from the adipose tissue of said HIV patient.

15. The method of claim 11, wherein said CD11b CD34$^-$CD45$^-$CD29$^+$CD49$^+$Oct4$^+$SSEA4$^+$stMSCs are isolated from the adipose tissue by collagenase digestion, but not including a plastic adherence selection step.

16. The method of claim 11, wherein said re-introducing step d) is by systemic injection.

17. The method of claim 11, wherein said re-introducing step d) is by surgical incision and placement.

18. The method of claim 11, wherein said CCR5$^-$CD11b$^-$CD34$^-$CD45$^-$CD29$^+$CD49$^+$Oct4$^+$SSEA4$^+$stMSCs are made with a CRISPR/CAS9 gene editing system.

19. The method of claim 18, wherein CRISPR/CAS9 gene editing system uses a guide RNA comprising a sequence selected from:
  i. SEQ ID NO. 1: TCACTATGCTGCCGCCCAGTGGG,
  ii. SEQ ID NO. 2: TCATCCTCCTGACAATCGATAGG,
  iii. SEQ ID NO. 3: CCTGACAATCGATAGGTACCTGG, and
  iv. SEQ ID NO. 4: CAATGTGTCAACTCTTGACAGGG.

20. The method of claim 11, wherein said CD11b$^-$CD34$^-$CD45 CD29$^+$CD49$^+$Oct4$^+$SSEA4$^+$stMSCs are isolated from the luminal side of the lamina elastica interna of the blood vessels of said HIV patient.

* * * * *